United States Patent [19]

Sparks et al.

[11] 4,076,981
[45] Feb. 28, 1978

[54] POSITION SENSITIVE AREA DETECTOR FOR USE WITH X-RAY DIFFRACTOMETER OR X-RAY CAMERA

[75] Inventors: Robert A. Sparks, Palo Alto; George B. Rothbart, Menlo Park; Roger N. Samdahl, San Jose, all of Calif.

[73] Assignee: Syntex (U.S.A.) Inc., Palo Alto, Calif.

[21] Appl. No.: 709,691

[22] Filed: Jul. 29, 1976

[51] Int. Cl.² .................................................. G01M 23/20
[52] U.S. Cl. ..................................... 250/272; 250/385
[58] Field of Search ......................... 250/272, 273, 385

[56] References Cited

U.S. PATENT DOCUMENTS

| 2,476,150 | 7/1949 | Koppius | 250/272 |
| 2,860,254 | 11/1958 | Hendee | 250/272 |
| 3,911,279 | 10/1975 | Gilland et al. | 250/385 |
| 3,975,639 | 8/1976 | Allemand | 250/385 |

*Primary Examiner*—Bruce C. Anderson
*Attorney, Agent, or Firm*—Joseph I. Hirsch; William B. Walker

[57] ABSTRACT

A position sensitive detector including a curved detector housing having a hollow detector chamber therein, the housing having an elongate opening in the curved side wall thereof and an x-ray transmissive material adjacent thereto to render the detector chamber airtight, a back cathode plane comprising a plurality of spaced cathode conductors on an insulator support and at least one curved anode wire, extending at least substantially transverse to the back cathode plane, disposed within the detector chamber in the path of x-rays entering through the elongate opening. Each anode wire, which is mechanically supported only at the ends thereof, is caused, during operation of the detector, to be supported in planar arcuate form solely by electrostatic forces. During operation of the detector, the chamber is filled with an ionizable gas and voltage is applied to the curved anode wire(s), thereby enabling detection of ionizing events occuring within the detector chamber.

The detector is particularly adapted to use with x-ray diffractometers, particularly of the powder type, but is also adapted for use with single crystal x-ray diffractometers and x-ray cameras.

28 Claims, 9 Drawing Figures

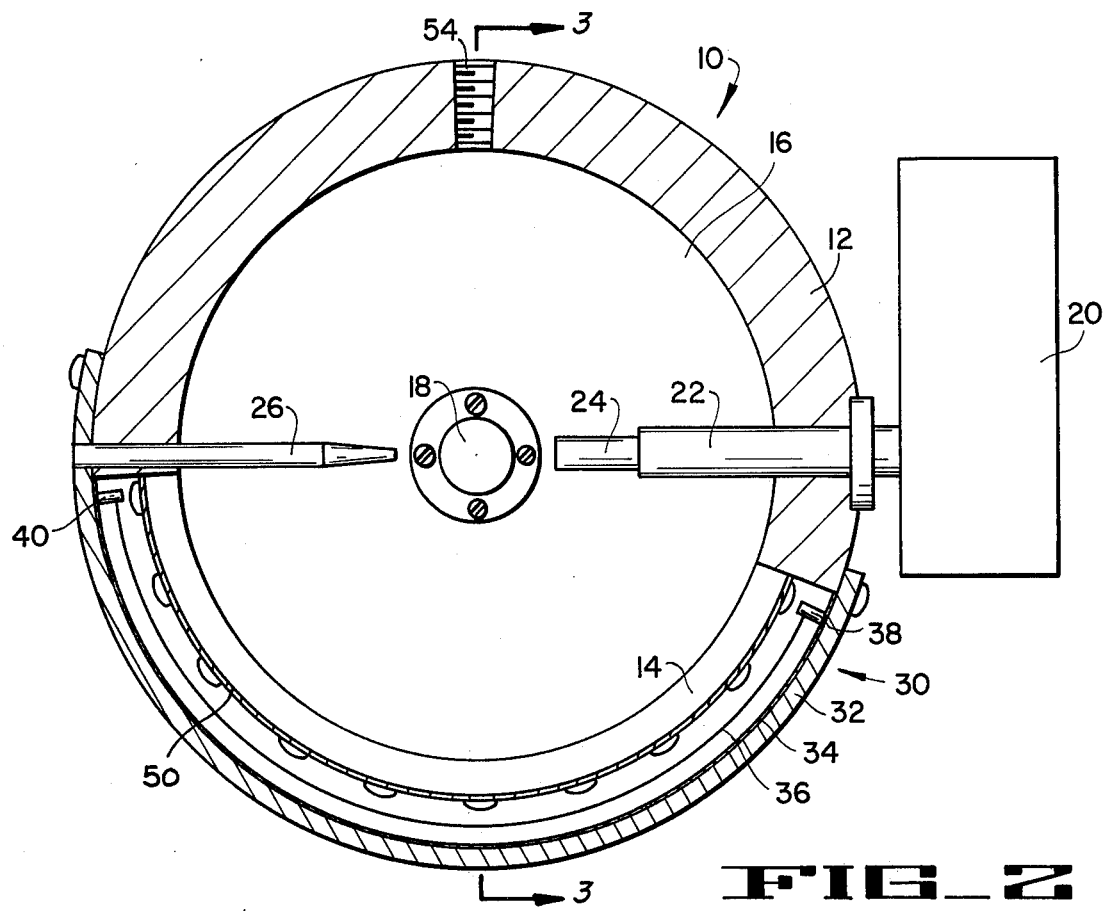
FIG_2
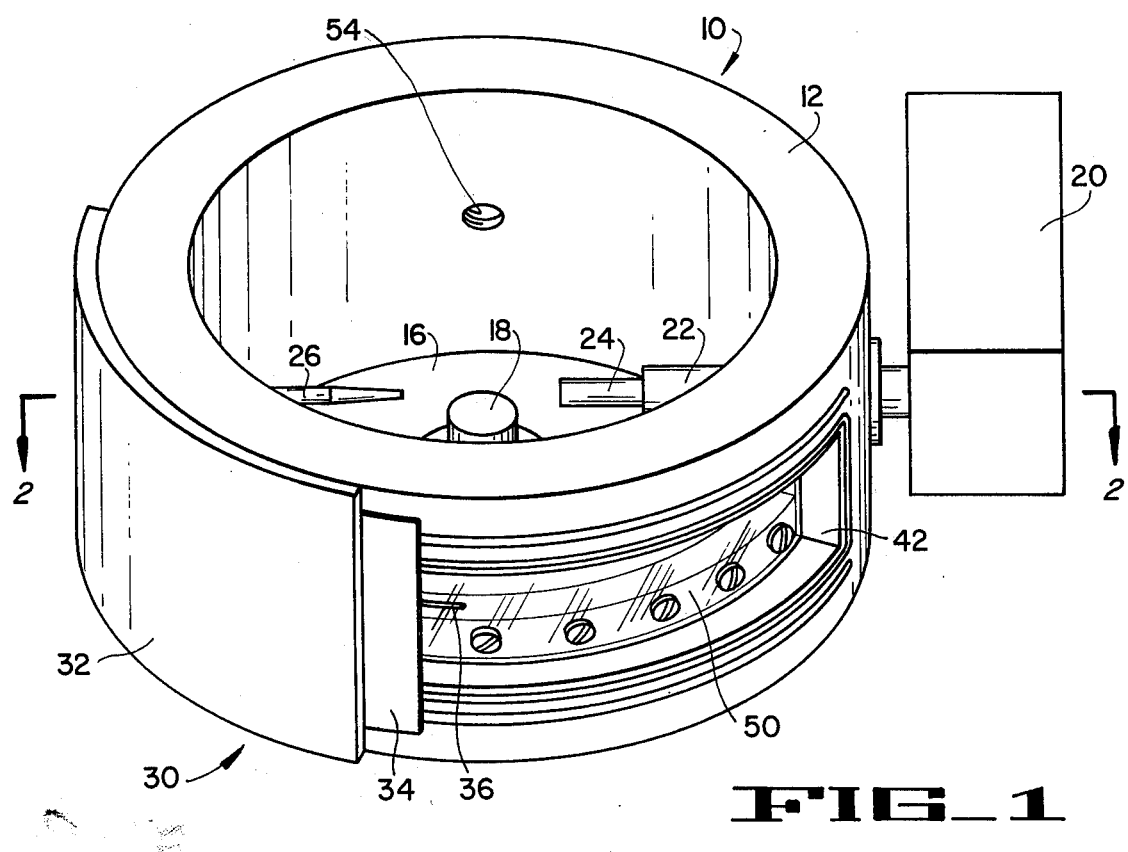
FIG_1

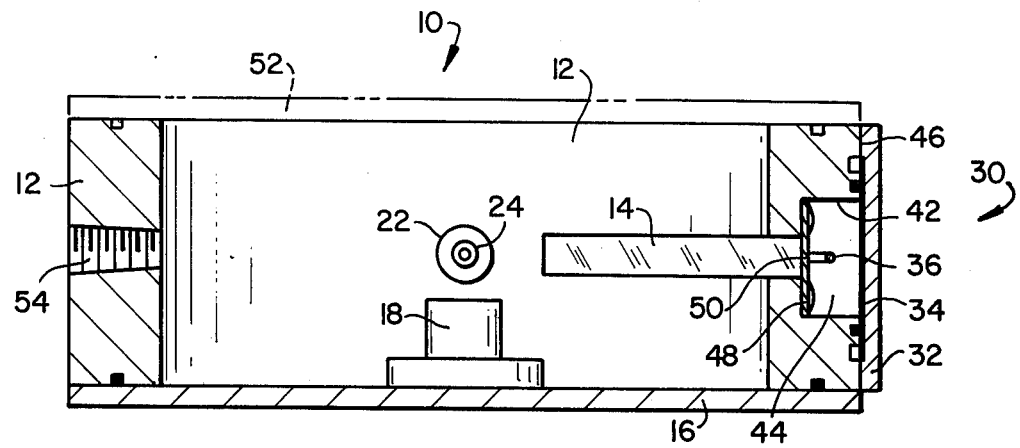
FIG_3
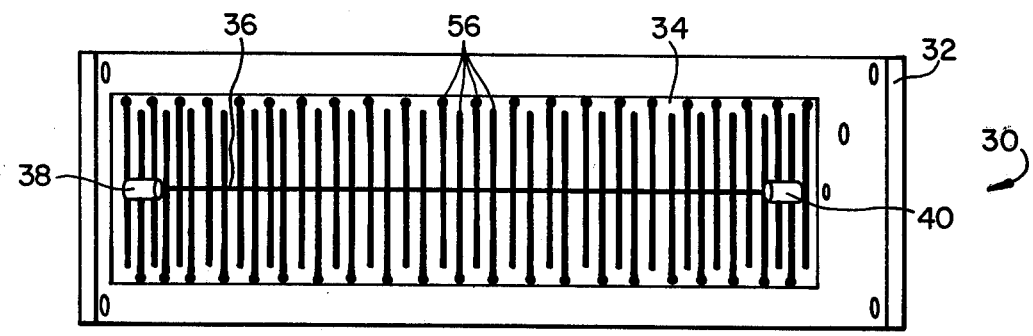
FIG_4
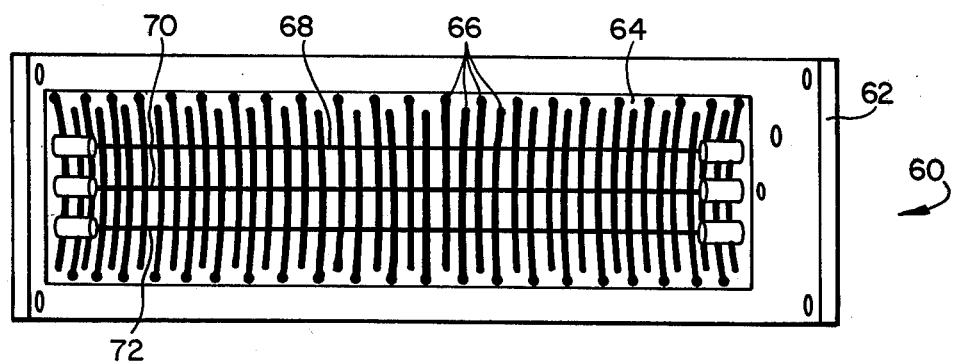
FIG_5

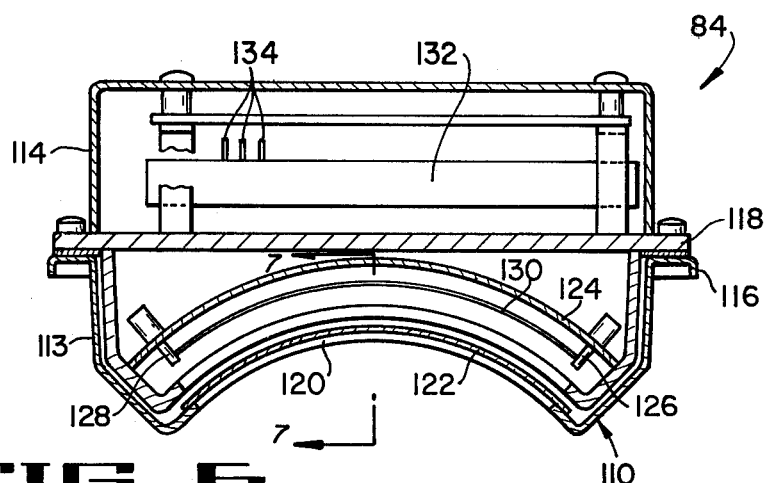
FIG_6
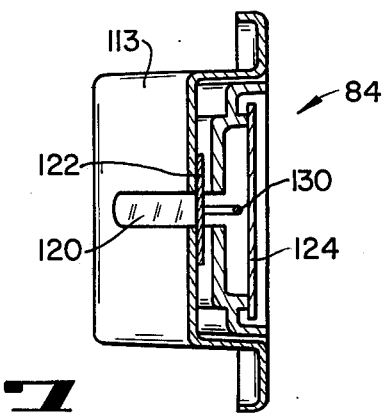
FIG_7
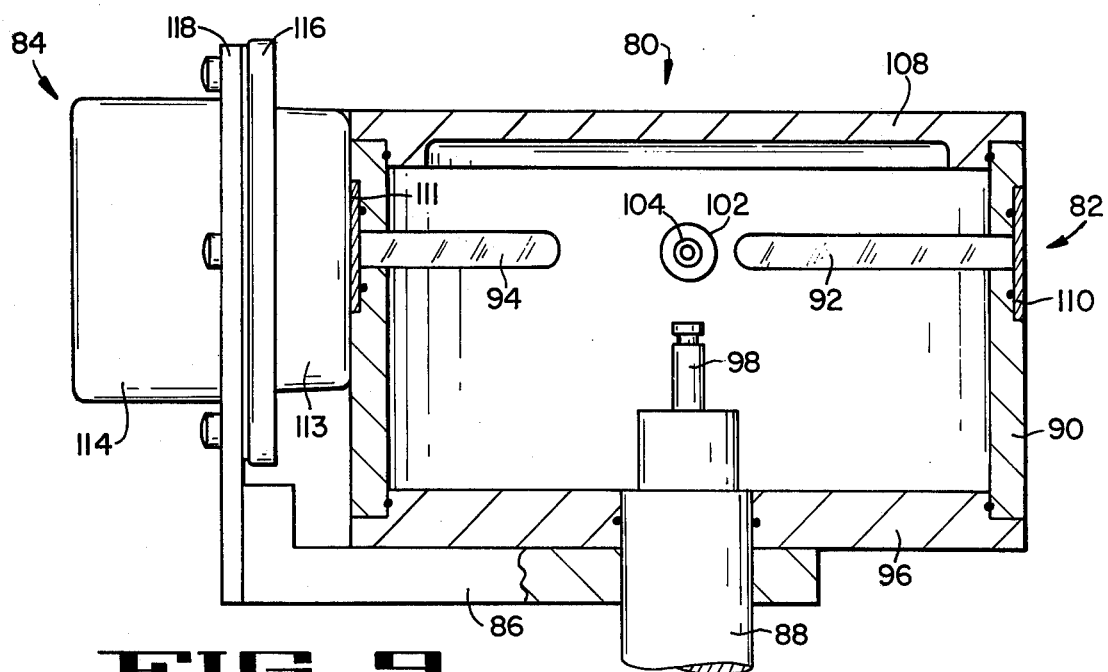
FIG_9

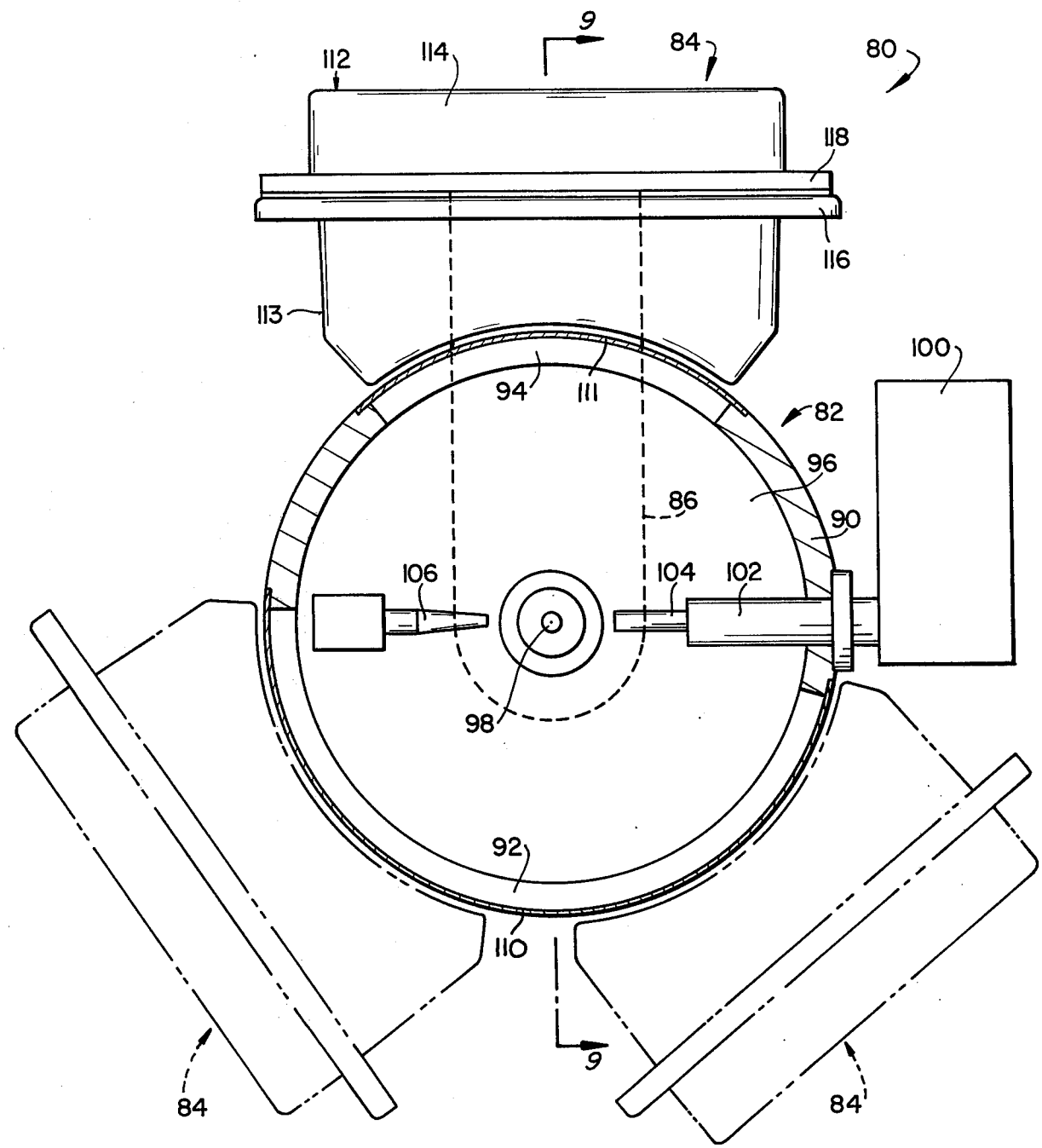
FIG_8

POSITION SENSITIVE AREA DETECTOR FOR USE WITH X-RAY DIFFRACTOMETER OR X-RAY CAMERA

FIELD OF THE INVENTION

This invention relates to position-sensitive detectors for simultaneously measuring diffraction patterns over a wide angle. More particularly, this invention relates to positionsensitive detectors adapted for use with x-ray diffractometers, particularly of the powder type, but also of the single crystal type, and with x-ray cameras.

BACKGROUND OF THE INVENTION

All existing x-ray powder cameras or x-ray diffractometers use x-ray sensitive photographic film or a single detector (e.g., a scintillation crystal with an associated photomultiplier tube) as the detection media. Film has the advantage that the whole pattern can be obtained at one time. The single detectors have the advantage of having much greater sensitivity that the photographic film inasmuch as they, in essence, detect all x-ray photons. Single detectors have the disadvantage, however, that because of their limited area of vision, they must scan the pattern in 2θ. As a result, the measurement with single detectors of powder patterns for small samples can take extremely long times (on the order of 24 hours for a 10μm sample). It would, accordingly, be desirable to have an improved detector for measuring radiation diffracted from a particular sample under analysis, particularly from a powdered sample.

OBJECTIONS OF THE INVENTION

It is, therefore, the primary object of this invention to provide a novel position-sensitive detector.

It is a further object of this invention to provide a novel position sensitive detector for simultaneously measuring diffraction patterns over a wide angle.

It is a further object of this invention to provide a novel position-sensitive detector for use with x-ray diffractometers and x-ray cameras.

It is a further object of this invention to provide an x-ray diffractometer or x-ray camera having the novel position-sensitive detector of this invention associated therewith.

These and still further objects, features and advantages of the present invention will become apparent upon consideration of the following detail disclosure.

SUMMARY OF THE INVENTION

These and still further objects, features and advantages of the present invention are achieved, in accordance therewith, by providing a position-sensitive detector having a curved detector housing having an elongate opening in a side wall thereof through which x-rays pass into the interior of the housing, a detector chamber within the interior of the detector housing, means to render the detector chamber air-tight, a curved back cathode plane disposed within the detector chamber opposite the elongate opening, the curved back cathode plane having a multiplicity of individual cathodes each comprising a spaced cathode conductor, at least one anode wire extending substantially transverse to the plane of the cathodes, each of the anode wire(s) being mechanically supported only at the ends thereof and otherwise being supported in planar arcuate form, during operation of the detector, solely by electrostatic forces.

In a first embodiment, the detector has an x-ray transmissive material, such as beryllium or mylar (i.e., polyethyleneterephthalate) disposed over the elongate opening. In this embodiment, the x-ray transmissive material is so placed as to cause the detector chamber to be rendered air-tight.

In a further embodiment, the detector housing is tightly abutted against a sample chamber or other housing in such a manner that the detector chamber is rendered air-tight. The sample chamber or housing has an x-ray transmissive material disposed between the sample being analyzed and the elongate opening in the side wall of the detector housing through which the diffracted x-rays pass so as to be detected by the detector.

The enclosed detector chamber must have an ionizable gaseous medium therein during operation of the detector. The detector chamber can be filled with the gaseous medium upon assembly of the detector, or means, such as input and output lines and associated valves, can be provided to fill and empty the detector chamber with the requisite gaseous medium as desired.

The detector further includes a delay line and associated electronic components, for example, means to apply a voltage to the anode wire(s), means for determining the position of each ionizing event caused by diffracted x-rays entering the detector chamber, and means for accumulating the signals from the plurality of ionizing events which occur so as to provide data from which the diffraction pattern of the sample being analyzed is determined over a wide angle.

The angular range over which data can be simultaneously detected, as by detecting the individual ionizing events, is approximately 30° to 90°, generally about 60° to about 70°, although smaller and larger angles can be utilized if desired and the particular configuration of the detector is designed to accommodate the curved anode wire(s) of greater angular range. Generally, however, where angular ranges of greater than approximately 70° are required, it is preferred to use a plurality of individual detectors or, optionally, a plurality of curved anode wire(s) which are disposed generally lengthwise around the perimeter of the angular range within which ionizing events are to be detected.

In a presently preferred embodiment, the detector of this invention, as described above, is used in combination with an air-tight sample chamber in which the sample is supported. The sample chamber has an elongate opening in the side wall thereof which is placed in juxtaposition with the elongate opening in the said wall of the detector housing so x-rays diffracted from the sample material can pass through the elongate opening in the side wall of the sample chamber, the elongate opening of the side wall in the detector housing and the x-ray transmissive material associated with such openings into the detector chamber within the interior of the detector housing where ionizing events occur and are detected by the back cathode plane, the curved anode wire(s) and the electronics associated therewith. If the elongate opening in the side wall of the sample chamber is of substantial angular range, for example on the order of about 180° to about 360°, the single detector of the type described herein can be moved to each of a plurality of different positions around the periphery of the sample chamber or, optionally, a plurality of detectors, of the type described herein, can be placed at different positions to simultaneously record diffracted patterns over a wide angle.

DESCRIPTION OF THE DRAWINGS

The foregoing and still further objects, features and advantages of the present invention will become more apparent from the following detailed description, taken together with the accompanying drawings wherein:

FIG. 1 is a perspective view, partially in section, of one embodiment of the detector of the present invention as placed adjacent a cylindrical sample chamber;

FIG. 2 is a horizontal cross-sectional view of the detector and sample chamber of FIG. 1 taken along line 2—2 of FIG. 1;

FIG. 3 is a vertical cross-sectional view of the detector and sample chamber of FIG. 1 taken along line 3—3 of FIG. 2;

FIG. 4 is a front elevational view of a portion of one embodiment of the detector of the present invention showing a curved back cathode plane and a single anode wire;

FIG. 5 is a front elevational view of a portion of a second embodiment of the detector of the present invention showing a different back cathode plane and a plurality (i.e., three) anode wires;

FIG. 6 is a top sectional view of an alternate embodiment of the detector of the present invention;

FIG. 7 is a side sectional view of the detector of FIG. 6 taken along line 7—7 of FIG. 6;

FIG. 8 is a top view, partially in section, of the sample chamber and the detector of FIG. 6, additionally showing alternative positions for the detector; and FIG. 9 is an elevational view, partially in section, taken along line 9—9 of FIG. 8.

Referring to FIGS. 1-3, there is shown, in schematic representation, a sampler chamber 10 defined, in part, by a cylindrical side wall 12 having an elongate opening 14 in one portion thereof. Base 16 forms the lower portion of sample chamber 10 and supports sample holder 18 which preferably can be rotated by means known in the art but not shown herein. X-rays from source 20 are directed toward the sample by collimator 22 (which passes through side wall 12) and collimator 24. On the opposite side of the sample from collimators 22 and 24 is beam stop 26. Detector 30 is in juxtaposition to elongate opening 14 in the side wall 12 of the sample chamber. Detector 30 includes, in this particular embodiment, an electrically insulating plate 32 supporting a back cathode plane 34 having a multiplicity of spaced cathode conductors thereon, a single curved anode wire 36 which is mechanically supported, at the ends thereof, by supports 38 and 40, respectively. Elongate opening 14 is counterbored as at 42 (see FIG. 3) so as to provide an air-tight detector chamber 44 between the outer surface 46 of side wall 12 (against which plane 34 abutts) and the inner surface 48 of the counterbore against which there is placed an x-ray transmissive material 50. Thus, in this embodiment, the sample chamber with its side wall having the elongate opening therein (including counterbore 42) also serve to define the detector housing and the detector chamber. Cover 52 (see FIG. 3) renders the sample chamber air-tight (although, in the strict sense, the chamber need not be air-tight, nor need there be any sample chamber at all, only a sample holder—in which case the detector per se must be of a different configuration to be described herein below). A vacuum can be drawn on the sample chamber and/or a gas mixture can be added to the sample chamber via port 54 having associated valve means (not shown). Chamber 44 is filled with a ionizable gaseous medium, such as argon or xenon, which, as indicated above can be caused to flow through the detector chamber during operation thereof, or can be added to the detector chamber at the time of assembly of the detector. X-rays diffracted from the sample (not shown) on sample holder 18 pass through elongate opening 14 and x-ray transmissive material 50 and cause ionizing events in detector chamber 44 which are detected by detector 30. Because of the particular configuration of the detectors of this invention, simultaneous electronic measurement of the diffracted x-ray patterns over a wide angle is achieved. Electrons generated during each ionizing event are attracted to the anode wire and induce a charge in one or more adjacent cathode conductors. The charge travels along the delay line, connected to the cathode conductors, and the time of arrival of a constant fraction (e.g., 30%) of peak maximum is detected and is a measure of the angular position of the charge-inducing ionizable event. These signals are accumulated by, for example, a mini-computer or a multi channel analyzer, for any given period of time to determine the intensity of the diffracted radiation as a function of angular position. The delay line and the associate electronics, and the mode of operation thereof to detect, determine and thus measure the position of each ionizing event, are well-known in this field and thus need not be described further.

Referring to FIG. 4, the portion of the detector 30 of FIGS. 1-3 is shown in greater detail and from a different perspective. Specifically, the plurality of spaced conductors 56 supported by back cathode plane 34 can readily be seen. As to be described in detail below, conductors 56 are connected to the delay line electronics associated with the detector so as to be able to detect the occurence and the positions of the various ionizing events occuring during sample analysis.

Referring to FIG. 5, there is shown an alternate embodiment 60 of a detector corresponding to the present invention. Particularly, detector 60 has insulator plate 62 supporting back cathode plane 64 upon which there is a multiplicity of spaced cathode conductors 66. In this configuration, the cathode conductors are positioned corresponding to the pattern of concentric rings which would be produced by cones of x-rays (diffracted from the sample) intersecting the surface of the back cathode plane. Thus, the spaced conductors are not vertical as shown in FIG. 4 but have some curvature thereto as shown in FIG. 5. Such curvature is dependent upon the particular geometry of the sample chamber and the associated detector of the present invention, and is particularly dependent upon the radius of curvature of the back cathode plane when considering the sample under analysis at the center of the circle. In addition, this embodiment also shows a plurality of anode wires 68, 70 and 72 which are extending substantially tranversely to the generally vertical dimension of the spaced cathode conductors 66. The detector of FIG. 5, accordingly, not only detects ionizing events along the longitudinal dimension of the detector (i.e., generally along curved anode wire 36 of FIG. 3) but also within a vertical (as shown) dimension by virtue of the placement of anode wires 68 and 72 above and below, respectively, anode wire 70.

Referring to FIGS. 6-9, there is shown, in schematic representation, an x-ray diffractometer 80 having a sample chamber 82 and a position-sensitive detector 84 which is supported by arm 86 about spindle 88 for rotatable movement about the cylindrical periphery of sample chamber 82. Sample chamber 82 is defined, in part, by a cylindrical side wall 90 having a first elongate opening 92 which extends on one side of the cylindrical wall for slightly less than 180° and a second elongate opening 94 which extends on the opposite portion of the side of the sample chamber for about 60°–70°. Base 96 forms the lower portion of sample chamber 82 and supports sample holder 98 which perferably can be rotated by means known in the art but not shown herein. X-rays from x-ray source 100 are directed toward the sample by collimator 102 (which passes through side wall 90) and collimator 104. On the opposite side of the sample from collimators 102 and 104 is beam stop 106. Top cover 108 and x-ray transmissive windows 110 and 111 associated with elongate openings 92 and 94, respectively, enable the interior of the sample chamber to be rendered air-tight.

As shown in FIG. 8, detector 84 is in juxtaposition, in this particular embodiment, to elongate opening 94 in the side wall 90 of the sample chamber. Detector 84 includes, in this particular embodiment, a detector housing 112 having a front portion 112 and a rear portion 114 which are bolted together at flanges 116 and 118, respectively. Front portion 113 of detector housing 112 has an elongate opening 120 and an x-ray transmissive material 122 disposed thereover to render the interior of the detector housing air-tight. Disposed within the interior of the detector housing is a curved back cathode plane 124 having a multiplicity of spaced cathode conductors (not shown) thereon. Also supported on back cathode plane 124 by insulator supports 126 and 128, respectively, is a single curved anode wire 130. As with the detector of FIGS. 1–3, the interior of the detector housing adjacent the curved anode wire and the back cathode plane is filled with an ionizable gaseous medium, such as argon or xenon. X-rays diffracted from the sample (not shown) on sample holder 98 pass through elongate opening 94 in the wall of the sample chamber, x-ray transmissive material 111 disposed over elongate opening 94, elongate opening 120 in the side wall of the detector housing and x-ray transmissive material 122 disposed thereover and cause ionizing events in the interior of the detector housing which are detected. Because of the particular configuration of the detectors of this invention, simultaneously electronic measurement of the diffracted x-ray patterns over a wide angle is achieved. Electrons generated during each ionizing event are attracted to the anode wire and induce a charge in one or more adjacent cathode conductors. Each cathode conductor is connected to delay line 132 via one of contacts 134. The charge induced in one or more of the cathode conductors travels along delay line 132 and the time of arrival of a constant fraction of peak maximum is detected in the associated electronics and is a measure of the angular position of the charge-inducing ionizing event. These signals are accumulated by, for example, a minicomputer or a multi-channel analyzer, for any given period of time to determine the intensity of the diffracted radiation as a function of angular position. As with the detector of FIGS. 1 $\propto$ 3, the delay line and the electronics associated therewith, and the mode of operation thereof, to detect and measure, and thus determine the position of each ionizing event, are well known in this field and will not be described further herein.

As indicated above, one of the particular advantages of this invention is that the detectors hereof can simultaneously detect and measure x-ray diffraction patterns over a wide angle. When it is desired to obtain information over an angle of approximately 180°, the detector can be positioned at a first position as shown in solid outline in FIG. 8 and then moved to the second and third positions shown in dotted outline in FIG. 8, or, alternatively, a detector can be positioned at each of the three positions shown for truly simultaneous measurement. This configuration makes use of the fact that the diffracted patterns are equivalent on opposite sides of a symmetrical sample chamber. Thus, those portions of a diffracted pattern which occur between the two detectors shown in dotted outline can be readily detected by the detector shown in solid outline on the opposite sides of the sample chamber. Overlapping data can be eliminated, to the extent necessary or desired, in the associated minicomputer or multi-channel analyzer, as would be apparent to one skilled in this art.

As described hereinabove, each of the curved anode wires is mechanically supported only at the ends thereof, but, during operation of the detectors described herein, assumes a planar, curved configuration due to the electrostatic forces existing between the wire and the adjacent back cathode plane. Where the detector has one anode wire, the anode wire and that portion of the back cathode plane which passes through the wire and the sample lie along concentric circles which have, as their center of curvature, the sample being analyzed. Where the detector has more than one anode wire, the back cathode plane and the anode wires will lie along concentric cylinders where the sample lies along the longitudinal axis of each cylinder. In either configuration, the back cathode plane will always be further from the sample than the anode wire(s).

Angular range, as used herein, refers to the angle between the sample being analyzed and the imaginary lines drawn from the sample to approximately each end of the anode wire (i.e., slightly to the inside of the insulator supports for the wire). Angular ranges of about 60°–70° can readily be achieved at arcs about 6 inches from the sample being analyzed; for arcs at greater distances, the angular range may be somewhat less, while at shorter distances, the angular range may be somewhat greater.

Angular resolution of the detectors described herein will be due, in part, to the spacing between adjacent cathode conductors, which can be on the order of 2mm or so. The anode wire(s) can be, for example, 30$\mu$ gold-plated tungsten wire.

During operation with a sample chamber, the sample chamber is preferably evacuated to a pressure on the order of 100 torr or less. The detector chamber can be filled with a 70% argon / 30% $CO_2$ mixture at 1 atmosphere which flows through the detector at the rate of about 1cf/hr.

Where second and third anode wires are used, as in the detector of FIG. 5, there are electrostatic forces existing not only between each anode wire and the back cathode plane but between the wires themselves. In such configurations, fourth and fifth wires can be placed above and below, respectively, the set of three wires (for example as shown in FIG. 5) to assist in maintaining the second and third wires in the desired planar arcuate form. Such fourth and fifth wires generally will be of larger diameter wire than the inner three anode wires to stabilize the electrostatic forces existing between the inner three wires and thereby maintain the second and third wires in the desired configuration.

The elongate opening in the wall of the sample chamber can be gradually reduced in dimension as it approaches 0° and 180° for the purpose of restricting the observed curvature of the diffracted radiation. This can be achieved by initially providing the desired configuration or by providing an aperture plate (having the desired opening configuration) which is placed adjacent to the side wall of the sample chamber having a more uniform opening as shown in the drawings hereof.

Optionally, opening 92 in sample chamber 82 of FIG. 8 can be replaced with two openings 92' and 92", each of the approximate angular range of opening 94, to achieve the same diffracted radiation information as with the device as shown. This can be done with either one, two or three detectors 84, as desired.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, design configuration or then-present objective to the spirit of this invention without departing from its essential teachings.

What is claimed is:

1. A position-sensitive detector adapted, during operation thereof, to hold an ionizable gasuous medium and suitable for use in detecting x-rays diffracted over a wide angle from a sample under analysis; said detector comprising housing having a hollow detector chamber therein, said housing having a curved side wall having an elongate opening therein, a back cathode plane and at least one anode wire spaced therefrom disposed within said detector chamber in the path of x-rays entering said detector chamber through said elongate opening, said back cathode plane comprising a plurality of spaced cathode conductors on an insulator support, each anode wire extending substantially transverse to the elongated dimension of said cathode conductors and being mechanically supported only at the ends thereof and otherwise being orientated in planar arcuate form, during operation of said detector, solely by electrostatic forces created by potential differences between each anode wire and said cathode conductors.

2. The detector of claim 1 wherein said curved side wall is defined by a side portion of a right cylinder.

3. The detector of claim 2 wherein said back cathode plane is curved, said curved back cathode plane being defined by a portion of a right cylinder having a greater radius of curvature than the radius of curvature of sad curved side wall.

4. The detector of claim 1 wherein said back cathode plane is curved.

5. The detector of claim 1 wherein there is one anode wire.

6. The detector of claim 1 wherein there are a plurality of separately supported anode wires.

7. The detector of claim 1 wherein there are three separately supported anode wires.

8. The detector of claim 1 wherein there are five separately supported anode wires, the outer anode wires being of larger diameter wire than the three inner anode wires.

9. The detector of claim 1 wherein said plurality of spaced cathode conductors extend substantially perpendicular to a plane which (a) is perpendicular to the surface of said back cathode plane and (b) passes through the sample to be analyzed.

10. The detector of claim 1 wherein there is one anode wire, and wherein said anode wire and that portion of said back cathode plane, which lies in the same plane as said anode wire and the sample being analyzed, lie along concentric circles which have, as the center of curvature, the sample being analyzed.

11. The detector of claim 1 wherein said detector has a plurality of separately supported anode wires, and said back cathode plane and said anode wires each lie along a side portion of imaginary concentric right cylinders where the sample being analyzed lies along the common longitudinal axis for each of said cylinders.

12. The detector of claim 1 wherein said detector chamber is air-tight.

13. The detector of claim 12 further including an x-ray transmissive material disposed adjacent to said elongate opening.

14. The detector of claim 12 further including an ionizable gaseous medium within said air-tight detector chamber.

15. The detector of claim 14 wherein said ionizable gaseous medium includes either argon or xenon.

16. The detector of claim 1 further including means to apply a potential to each of said anode wires.

17. The detector of claim 1 further including means associated with said detector for determining the intensity of radiation diffracted from the sample as a function of angular position.

18. The detector of claim 17 wherein said means for determining the intensity of radiation diffracted from the sample as a function of angular position includes a delay line and electronic means associated therewith for detecting, determining and measuring the angular position of each ionizing event caused by x-rays entering said detector chamber through said elongate opening.

19. The detector of claim 1 in combination with means for holding a sample to be analyzed and x-ray source means for directing a beam of x-radiation at a sample held by said sample holding means.

20. The combination of claim 19 wherein said sample holding means is positioned within an air-tight sample chamber, said sample chamber having an elongate opening in a side wall thereof and an x-ray transmissive material associated therewith to maintain said sample chamber air-tight, said elongate opening in the side wall of said sample chamber being adapted for placement in juxtaposition with said elongate opening in the side wall of said detector chamber.

21. The detector of claim 1 in combination with an air-tight sample chamber having a cylindrical side wall, means within said sample chamber for holding a sample to be analyzed, x-ray source means for directing a beam of x-radiation at a sample held by said sample holding means, said sample chamber having first and second elongate openings in the cylindrical side wall thereof which are adapted for placement in juxtaposition with said elongate opening in the side wall of said detector chamber, one of said elongate openings in the side wall of said sample chamber extending for about 180° around the periphery of said sample chamber from about the point where the x-ray radiation enters said sample chamber to approximately the point where it would exit from said sample chamber if not diffracted by the sample being analyzed, the other elongate opening in the side wall of said sample chamber being on the opposite side of the cylindrical side wall from said first elongate opening, said first and second elongate openings being of such placement and configuration that substantially all of the desired diffracted radiation information from the sample being analyzed can be determined by placement of one or more detectors adjacent said elongate openings and detecting the diffracted radiation passing therethrough.

22. A position-sensitive detector adapted, during operation thereof, to hold an ionizable gasuous medium and suitable for use in detecting x-rays diffracted over a wide angle from a sample under analysis; said detector comprising housing having a hollow detector chamber therein, said housing having a curved side wall defined by a side portion of a right cylinder, said curved side wall having an elongate opening therein, a curved back cathode plane disposed within said detector chamber in the path of x-rays entering said detector chamber through said elongate opening, said curved back cathode plane being defined by a side portion of a right cylinder having a greater radius of curvature than the radius of curvature of said curved side wall, said back cathode plane comprising a plurality of spaced cathode conductors on an insulator support, said plurality of spaced cathode conductors extending substantially perpendicular to a plane which (a) is perpendicular to the surface of a said back cathode plane and (b) passes through the sample to be analyzed, at least one anode wire spaced between said back cathode plane and said elongate opening also in the path of x-rays entering said detector chamber through said elongate opening, each anode wire extending substantially transverse to the elongated dimension of said cathode conductors and being mechanically supported only at the ends thereof and otherwise being orientated in planar, cylindrically curved form, during operation of said detector, solely by electrostatic forces created by potential differences between each anode wire and said cathode conductors.

23. The detector of claim 22 wherein there is one anode wire, and wherein said anode wire and that portion of said back cathode plane which lie in the same plane as said anode wire and the sample being analyzed, lie along concentric circles which have, as the center of curvature, the sample being analyzed.

24. The detector of claim 22 further including an x-ray transmissive material disposed adjacent said elongate opening to render said detector chamber air-tight.

25. The detector of claim 24 further including an ionizable gaseous medium within said air-tight chamber.

26. The detector of claim 25 in combination with means to apply a potential to each of said anode wires and means associated with said detector for determining the intensity of radiation diffracted from the sample as a function of angular position.

27. The combination of claim 26 wherein said means for determining the intensity of radiation diffracted from the sample as a function of angular position includes a delay line connected to said plurality of spaced cathode conductors, means associated with said delay line for determining the angular position of each ionizing event caused by x-rays entering said detector chamber through said elongate opening, and means for accumulating the signals from the plurality of ionizing events which occur whereby data is provided from which the diffraction pattern of the sample being analyzed can be determined over a wide angle.

28. The detector of claim 21 wherein said elongate opening which extends for about 18° around the periphery of said sample chamber has an effective opening which is gradually reduced in dimension as said elongate opening approaches 0° and 180°.

* * * * *